US012788705B2

(12) United States Patent
Schmid et al.

(10) Patent No.: US 12,788,705 B2
(45) Date of Patent: Nov. 10, 2026

(54) HAIR TREATMENT COMPOSITION

(71) Applicant: KAO GERMANY GMBH, Darmstadt Hessen (DE)

(72) Inventors: Sabine Schmid, Darmstadt (DE); Britta Punsch, Darmstadt Hessen (DE)

(73) Assignee: KAO GERMANY GMBH, Darmstadt Hessen (DE)

( * ) Notice: Subject to any disclaimer, the term of this patent is extended or adjusted under 35 U.S.C. 154(b) by 192 days.

(21) Appl. No.: 17/258,959

(22) PCT Filed: Jul. 15, 2019

(86) PCT No.: PCT/EP2019/068950
§ 371 (c)(1),
(2) Date: Jan. 8, 2021

(87) PCT Pub. No.: WO2020/016148
PCT Pub. Date: Jan. 23, 2020

(65) Prior Publication Data

US 2021/0338563 A1 Nov. 4, 2021

(30) Foreign Application Priority Data

Jul. 16, 2018 (EP) .................................... 18183698

(51) Int. Cl.
*A61K 8/92* (2006.01)
*A61K 8/02* (2006.01)
(Continued)

(52) U.S. Cl.
CPC ................ *A61K 8/927* (2013.01); *A61K 8/23* (2013.01); *A61K 8/342* (2013.01); *A61K 8/8111* (2013.01);
(Continued)

(58) Field of Classification Search
CPC .......... A61K 8/927; A61K 8/23; A61K 8/342; A61K 8/8111; A61K 8/8135;
(Continued)

(56) References Cited

U.S. PATENT DOCUMENTS 6,153,204 A * 11/2000 Fanger .................. A61Q 19/00 424/68
6,528,073 B2 * 3/2003 Roulier .................. A61K 8/733 424/70.6
(Continued)

FOREIGN PATENT DOCUMENTS

EP 2394631 A1 12/2011
EP 3597172 A1 1/2020
(Continued)

OTHER PUBLICATIONS

International Search Report mailed Oct. 7, 2019, in connection with PCT International Application No. PCT/EP2019/068950.
(Continued)

*Primary Examiner* — Trevor Love
*Assistant Examiner* — Janet Joseph
(74) *Attorney, Agent, or Firm* — Norris McLaughlin, PA

(57) ABSTRACT

Present invention relates to a substantially anhydrous composition comprising suspended particles insoluble therein for conditioning and/or styling hair. The composition for hair comprises one or more fatty substances and/or waxes solid at 20° C., one or more surfactants and calcium sulphate powder, with the condition that the composition does not comprise water at a concentration more than or equal to 5% by weight, calculated to the total of the composition.

9 Claims, 1 Drawing Sheet

(51) Int. Cl.

| | |
|---|---|
| ***A61K 8/19*** | (2006.01) |
| ***A61K 8/23*** | (2006.01) |
| ***A61K 8/31*** | (2006.01) |
| ***A61K 8/34*** | (2006.01) |
| ***A61K 8/81*** | (2006.01) |
| ***A61K 8/86*** | (2006.01) |
| ***A61Q 5/06*** | (2006.01) |
| ***A61Q 5/12*** | (2006.01) |

(52) U.S. Cl.
CPC .......... *A61K 8/8135* (2013.01); *A61K 8/8176* (2013.01); *A61K 8/86* (2013.01); *A61K 8/922* (2013.01); *A61Q 5/06* (2013.01); *A61Q 5/12* (2013.01); *A61K 2800/31* (2013.01); *A61K 2800/594* (2013.01); *A61K 2800/596* (2013.01)

(58) Field of Classification Search
CPC ........ A61K 8/8176; A61K 8/86; A61K 8/922; A61K 2800/31; A61K 2800/594; A61K 2800/596; A61K 2800/651; A61K 8/31; A61K 8/19; A61K 8/0241; A61Q 5/06; A61Q 5/12
See application file for complete search history.

(56) References Cited

U.S. PATENT DOCUMENTS

| | | | | |
|---|---|---|---|---|
| 7,431,918 | B2 * | 10/2008 | Shelley | A61K 8/0241 424/401 |
| 8,372,160 | B2 * | 2/2013 | Wood | A61Q 5/08 8/405 |
| 2003/0003161 | A1 | 1/2003 | Van Scoik et al. | |
| 2004/0062778 | A1 | 4/2004 | Shefer et al. | |
| 2005/0163738 | A1 * | 7/2005 | Loifenfeld | A61Q 5/06 424/70.12 |
| 2008/0089855 | A1 * | 4/2008 | Walter | A61K 8/922 424/70.11 |
| 2008/0118456 | A1 * | 5/2008 | Brautigam | A61P 43/00 424/70.13 |
| 2016/0143827 | A1 * | 5/2016 | Castan Barberan | A61K 8/0216 424/70.1 |
| 2017/0000700 | A1 * | 1/2017 | Pratt | A61K 8/447 |
| 2017/0319876 | A1 * | 11/2017 | Hentrich | A61Q 5/12 |

FOREIGN PATENT DOCUMENTS

| | | | |
|---|---|---|---|
| EP | 3823583 | A1 | 5/2021 |
| JP | 2017-149705 | A | 8/2014 |
| JP | 2014162788 | A | 9/2014 |
| KR | 20060039594 | A | 5/2006 |
| KR | 20100071839 | A | 6/2010 |
| WO | 98/20103 | A1 | 5/1998 |

OTHER PUBLICATIONS

Written Opinion issued in connection with PCT International Application No. PCT/EP2019/068950.
European Office Action dated Oct. 2, 2022, in connection with European Application No. 19 737 553.8.
European Extended Search Report dated Dec. 18, 2014, in connection with European Application No. 18183698.2.
EP19737553.8—Communication Pursuant to Article 94(3) EPC, mailed on Dec. 19, 2025, 4 pages.

* cited by examiner

A B C
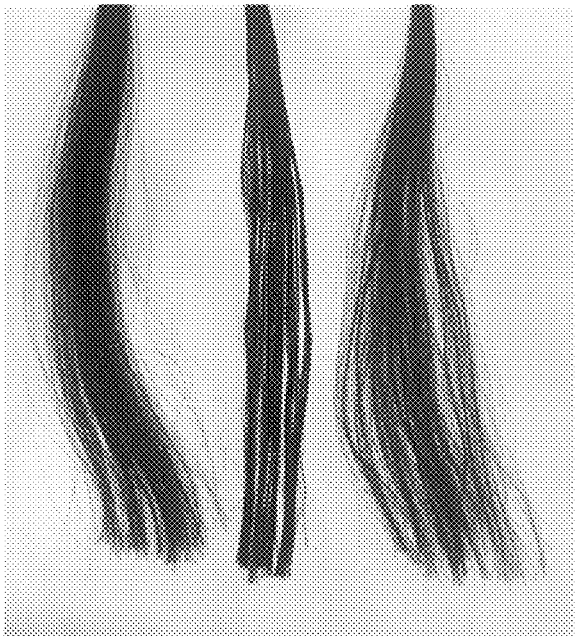

HAIR TREATMENT COMPOSITION

This application is the U.S. National Stage of International Application No. PCT/EP2019/068950, filed Jul. 15, 2019, which claims foreign priority benefits under 35 U.S.C. § 119 of European Application Nos. 18183698.2, filed Jul. 16, 2018, the disclosure of which is incorporated herein by reference.

Present invention relates to a substantially anhydrous composition comprising suspended particles insoluble therein for conditioning and/or styling hair.

Gels based on thickening and styling polymers have been widely used for styling hair by fixing the hair in a shape. These compositions make hair hard and stiff which is not always preferred by the consumers. Instead, these consumers prefer using waxes and pastes to condition and style their hair which does not make hair hard and stiff, but then causes aggregation of single hair fibres. The hair treated with such compositions appears streaky and including too many hair fibre aggregates which take away cosmetic and attractive appearance.

In order to prevent hair fibre aggregation, inert particulate material is usually added to the compositions, which absorbs fatty substances. Kaolin and Diatomaceous Earth are usually used for this purpose. However, the results are not satisfactory as their fatty substance sorption capacity is very limited and, therefore, hair treated with such compositions still comprises plenty of hair fibre aggregates and does still not have the targeted attractive appearance. Therefore, there is highly need for new compositions which overcome the aforementioned disadvantageous.

The inventors of the present invention have unexpectedly found out that a substantially anhydrous composition comprising wax, surfactant and calcium sulphate particles dispersed therein provides good conditioning and styling effects and provides hair attractive appearance as hair fibres, in a greater extent, are not aggregated and appear loosely.

Thus, the first object of the present invention is a composition for hair comprising one or more fatty substances and/or waxes solid at 20° C., one or more surfactants and calcium sulphate powder, with the condition that the composition does not comprise water at a concentration more than or equal to 5% by weight, calculated to the total of the composition.

Further object of the present invention is the use of the composition for conditioning and/or styling hair.

The compositions are used as leave in compositions and not rinsed off from hair after application. Thus, another object of the present invention is process for conditioning and/or styling hair wherein the composition is applied onto dry hair and not rinsed off from hair.

BRIEF DESCRIPTION OF THE DRAWING

FIG. 1 is a photograph of hair streaks comprising an untreated streak. a streak treated with the comparative composition. and a streak treated with the Example 1.

DETAILED DESCRIPTION OF THE DISCLOSURE

The composition of the present invention is preferably provided to the users, consumers, in the form of a kit. Therefore, further object of the present invention is a kit for hair comprising the composition of the present invention.

The composition is substantially anhydrous and principally does not comprise any added water and therefore the water content of the composition may not be higher or equal to 5% by weight, preferably 3% by weight and more preferably 1% by weight calculated to the total of the composition. In a particularly preferred embodiment, the composition is anhydrous, in case anhydrous ingredients may be used.

Within the meaning of the present invention, the fatty substances and waxes are compounds with a melting point above 20° C., preferably above 30° C. and more preferably above 35° C. Suitable ones are petrolatum, ozokerit, carnauba wax, paraffin, lanolin wax, candelila wax, bees wax, microcrystalline wax, fatty alcohols and their mixtures. It should be noted that ethoxylated and/or propoxylated waxes are taken as waxes and not as surfactants.

Suitable fatty alcohols are such as cetyl alcohol, stearyl alcohol, myristyl alcohol, behenyl alcohol and their mixtures.

The preferred fatty substances and waxes are beeswax, petrolatum, ozokerit, carnauba wax, cetearyl alcohol and their mixtures.

The composition comprises the one or more fatty substances and/or waxes at a total concentration of 10 to 70% by weight, preferably 15 to 65% by weight, more preferably 20 to 65% by weight, most preferably 25 to 65% by weight calculated to the total of the composition.

The composition of the present invention comprises at least one surfactant, preferably selected from anionic and non-ionic surfactants. Non-ionic surfactants are especially preferred.

Suitable non-ionic surfactants are fatty alcohol ethoxylates, monoglycerides and their ethoxylates, ethoxylated oils, long-chain fatty acid mono- and dialkanolamides, alkyl polyglucosides and sorbitan esters. Fatty alcohol ethoxylates, monoglycerides and their ethoxylates, ethoxylated oils are the preferred ones.

Suitable monoglycerides are glycerin fatty acid esters with an acyl chain length of 8 to 24 C atoms which may be straight or branched and may have one or more substitutions, such as glyceryl stearate, palmitate, behenate, myristate, oleate, laurate, caprylate, etc. which may further be ethoxylted and/or propoxylated.

Suitable ethoxylated fatty acids with an acyl chain length of 12 to 24 C atoms are PEG-20 stearate, PEG-23 stearate, PEG-25 stearate, PEG-30 stearate, PEG-32 stearate, PEG-35 stearate, PEG-36 stearate, PEG-40 stearate, PEG-45 stearate, PEG-50 stearate, PEG-55 stearate, PEG-75 stearate, PEG-80 stearate, PEG-90 stearate, PEG-100 stearate, PEG-120 stearate, PEG-150 stearate, PEG-20 oleate, PEG-23 oleate, PEG-32 oleate, PEG-36 oleate, PEG-75 oleate, PEG-150 oleate, PEG-10 laurate, PEG-12 laurate, PEG-14 laurate, PEG-20 laurate, PEG-32 laurate, PEG-75 laurate, PEG-150 laurate, PEG-18 palmitate, and PEG-20 palmitate.

Suitable fatty alcohol ethoxylates are $C_{10}$-$C_{22}$-fatty alcohol ethoxylates. Especially suited are $C_{10}$-$C_{22}$-fatty alcohol ethers, the alkyl polyglycol ethers known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16": The average degree of ethoxylation thereby ranges between about 2.5 and about 100, preferably about 10 and about 50. Suitable non-limiting examples are Laureth-10, Laureth-11, Laureth-12, Laureth-13, Laureth-14, Laureth-15, Laureth-16, Laureth-20, Laureth-21, Laureth-23, Laureth-25, Laureth-30, Laureth-38, Laureth-40, Laureth-50, Laureth-100, Myreth-10, Ceteth-10, Ceteth-12, Ceteth-13, Ceteth-14, Ceteth-15, Ceteth-16, Ceteth-17, Ceteth-18, Ceteth-20, Ceteth-23, Ceteth-24, Ceteth-25, Ceteth-30, Ceteth-40, Ceteth-45, Ceteth-150, Cetoleth-10, Cetoleth-11, Cetoleth-15, Cetoleth-18, Cetoleth-20, Cetoleth-22, Cetoleth-24, Cetoleth-25, Cetoleth-30, Oleth-10, Oleth-11, Oleth-12, Oleth-15, Oleth-16, Oleth-20, Oleth-23, Oleth-24, Oleth-25, Oleth-30, Oleth-35, Oleth-40, Oleth-44, Oleth-45, Oleth-50, Oleth-82, Oleth-100, Steareth-10, Steareth-11, Steareth-12, Steareth-13, Steareth-14, Steareth-15, Steareth-16, Steareth-20, Steareth-21, Steareth-25, Steareth-30, Steareth-40, Steareth-50, Steareth-80, Steareth-100, Ceteareth-10, Ceteareth-11, Ceteareth-12, Ceteareth-13, Ceteareth-14, Ceteareth-15, Ceteareth-16, Ceteareth-17, Ceteareth-18, Ceteareth-20, Ceteareth-22, Ceteareth-23, Ceteareth-24, Ceteareth-25, Ceteareth-27, Ceteareth-28, Ceteareth-29, Ceteareth-30, Ceteareth-33, Ceteareth-34, Ceteareth-40, Ceteareth-50, Ceteareth-55, Ceteareth-60, Ceteareth-80 and Ceteareth-100.

Further suitable nonionic surfactants are ethoxylated oils such as ethoxylated hydrogenated castor oil with 40 and 60 ethoxy units, ethoxylated olive oil with 5 to 60 ethoxy units, ethoxylated coconut oil with 5 to 60 ethoxy units and ethoxylated sunflower oil with 5 to 60 ethoxy units.

Further suitable non-ionic surfactants are alkyl polyglucosides of the general formula $$R_{12}\text{—O—}(R_{13}O)_n\text{O—}Z_x$$

wherein $R_{12}$ is an alkyl group with 8 to 18 carbon atoms, $R_{13}$ is an ethylene or propylene group, Z is a saccharide group with 5 to 6 carbon atoms, n is a number from 0 to 10 and x is a number between 1 and 5. Examples are decyl polyglucoside, cocoyl polyglucoside both are commercially available.

Further suitable non-ionic surfactant components are, for example, long-chain fatty acid mono- and dialkanolamides, such as coco fatty acid monoethanolamide and myristic fatty acid monoethanolamide.

Further additionally useful non-ionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics$^R$".

Among the non-ionic surfactants mentioned above fatty alcohol ethoxylates, ethoxylated oils and monoglycerides and their ethoxylates and their mixtures are the most preferred ones.

Anionic surfactants suitable are alkyl sulfates, alkyl ether sulfates, alkyl polyether carboxylic acids, amino carboxylate and phosphate surfactants.

Suitable sulphate surfactants are according to the general structure $$R_1(OCH_2CH_2)_nOSO_3M$$

wherein R is an alkyl chain which may be saturated or unsaturated, straight or branched with 10 to 22 C atoms, preferably 12 to 20 and more preferably 12 to 18 and most preferably 12 to 16 C atoms, n is a number between 0 and 5 and M is a cation and preferably sodium, potassium or ammonium, more preferably sodium or ammonium. Suitable examples are alkyl sulphates such as sodium lauryl sulphate, sodium cetyl sulphate, sodium stearyl sulphate and alkyl ether sulphates such as sodium laureth sulphate, sodium myreth sulphate, sodium ceteth sulphate, sodium oleth sulphate, sodium steareth sulphate, ammonium laureth sulphate, ammonium myreth sulphate, ammonium oleth sulphate, ammonium ceteth sulphate, ammonium steareth sulphate.

Suitable surfactants of the carboxylate type are alkyl polyether carboxylic acids and the salts thereof of the formula $$R_2\text{—}(C_2H_4O)_n\text{—O—}CH_2COOX,$$

wherein $R_9$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted.

Suitable anionic amino carboxylate surfactants are also $C_8$-$C_{22}$-acyl aminocarboxylic acids or the water-soluble salts thereof, such as N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in mixture with the above-named anionic surfactants.

Suitable phosphate surfactants are the ones according to general structure $$(R_3(OC_2H_4)_x(OC_3H_6)_yO)_3PO$$

wherein $R_3$ is an alkyl chain which may be saturated or unsaturated branched or straight with 8 to 22 C atoms, preferably 10 to 18 C atoms and more preferably 12 to 16 C atoms, x and y are in the range of 0 to 10 with the condition x+y is more than 0. Suitable non-limiting example is Trilaureth-4 phosphate and its salts.

The composition comprises one or more surfactants at a total concentration in the range of 2 to 35% by weight, preferably 5 to 30% by weight, and more preferably 5 to 25% by weight and most preferably 7.5 to 22% by weight, calculated to the total of the composition.

The composition comprises powder calcium sulphate at a concentration in the range of 2 to 35% by weight, preferably 5 to 30% by weight, and more preferably 5 to 25% by weight and most preferably 7.5 to 22% by weight, calculated to the total of the composition.

In a preferred embodiment of the present invention, the calcium sulphate powder has a particle size below 200 μm measured with sieve analysis.

In a further preferred embodiment of the present invention, the compositions comprise one or more additional inert pulverulent material dispersed therein. Suitable ones are Diatomaceous Earth, kaolin, silicium dioxide, starch such as wheat, rice, potato and corn, and titan dioxide. Diatomaceous Earth and kaolin are the preferred ones and the Diatomaceous Earth is the most preferred.

The total concentration of the additional inert pulverulent material is in the range of 2 to 35% by weight, preferably 5 to 30% by weight, and more preferably 5 to 25% by weight and most preferably 7.5 to 22% by weight, calculated to the total of the composition.

In a further preferred embodiment the compositions of the present invention comprises one or more hair styling polymers selected from anionic, cationic, non-ionic and amphoteric ones.

Suitable non-ionic polymer is first of all vinylpyrrolidon polymers either homopolymers or copolymers with, especially, vinylacetate. Those are known with the trade name "Luviskol" as homopolymers Luviskol K 30, K 60 or K 90 as well copolymers Luviskol VA 55, VA 64, Plus from BASF AG.

Natural non-ionic polymers are as well suitable for the composition of the present invention. Those are such as cellulose, chitosan, guar gum and their derivatives.

As amphoteric polymers which can be used alone or in mixture with at least one additional nonionic polymer, reference is here made in particular to copolymers of N-octyl acrylamide, (meth)acrylic acid and tert.-butyl aminoethyl methacrylate of the type "Amphomer®", copolymers from methacryloyl ethyl betaine and alkyl meth-acrylates of the type "Yukaformer®", e.g.. the butyl methacrylate copolymer "Yukaformer® Am75"; copolymers from monomers containing carboxyl groups and sulfonic groups, e.g. (meth) acrylic acid and itaconic acid, with monomers such as mono- or dialkyl aminoalkyl (meth)acrylates or mono- or dialkyl aminoalkyl (meth)-acrylamides containing basic groups, in particular amino groups; copolymers from N-octyl acrylamide, methyl methacrylate, hydroxypropyl methacrylate, N-tert.-butyl aminoethyl methacrylate and acrylic acid, as well as the copolymers known from U.S. Pat No. 3,927,199.

Suitable anionic polymers alone or in combination with non-ionic polymers are vinyl-alkyl ether, in particular methyl vinyl ether/maleic acid copolymers, obtained by hydrolysis of vinyl ether/maleic anhydride copolymers, distributed under the trade name "Gantrez® AN or ES". These polymers may also be partly esterified, as for example, "Gantrez® ES 225" or "ES 435", the ethyl ester of an ethyl vinyl ether/maleic acid copolymer, or the butyl or isobutyl ester thereof.

Further useful anionic polymers are in particular vinyl acetate/crotonic acid or vinyl acetate/vinyl neodecanoate/crotonic acid copolymers of the type "Resyn®"; sodium acrylate/vinyl alcohol copolymers of the type "Hydagen® F", sodium polystyrene sulfonate, e.g.. "Flexan® 130"; ethyl acrylate/acrylic acid/N-tert.-butyl acrylamide co-polymers of the type "Ultrahold®"; vinyl pyrrolidone/vinyl acetate/itaconic acid co-polymers, acrylic acid/acrylamide copolymers or the sodium salts thereof of the type "Reten®"; etc.

Further suitable anionic polymers are Acrylate copolymers available under trade name Salcare SC 81, PEG/PPG 25/25 dimethicone/acrylate copolymer available under trade name Luvigel Silk from BASF, Acrylates/t-butylacrylamide copolymer available under trade name Ultrahold Strong, Advantage LC-E which is vinylcaprolactam/PVP/dimethylaminoethylmethacrylate copolymer and VA/crotonates copolymer available under trade name Luviset CA 66.

Suitable cationic polymers are those known with their CTFA category name Polyquaternium. Typical examples of those are Polyquaternium-6, Polyquaternium-7, Polyquaternium-10, Polyquaternium-11, Polyquaternium-16, Polyquaternium-22 and Polyquaternium- 28, Polyquaternium-30, Polyquaternium-37, Polyquaternium-36, Polyquaternium-46, Polyquaternium-24, Polyquaternium-67, and Polyquaternium-72.

In this context, reference is also made to the cationic polymers disclosed in DE 25 21 960, 28 11 010, 30 44 738 and 32 17 059, as well as to the products described in EP-A 337 354 on pages 3 to 7, It is also possible to use mixtures of various cationic polymers.

The cationic polymers also include the quaternized products of graft polymers from organopolysiloxanes and polyethyl oxazolines described in EP-A 524 612 and EP-A 640 643. Among these especially preferred is the compound know with the INCI name Polysilicone-9.

The compositions comprise one or more hair styling polymers at a total concentration in the range of 0.1 to 25% by weight, preferably 1.5 to 20% by weight, more preferably 2.5 to 15% by weight and most preferably 4 to 15% by weight calculated to the total of the composition.

In a further embodiment of the present invention, the composition may comprise one or more synthetic and/or natural oil. In principal, any oil allowed for cosmetic use is suitable for the compositions of the present invention.

Oils are those of synthetic and of natural ones. Natural oils are in principal any triglyceride suitable for cosmetic use. Non-limiting examples are avocado oil, coconut oil, palm oil, sesame oil, peanut oil, sunflower oil, almond oil, peach kernel oil, wheat germ oil, macadamia nut oil, night primrose oil, jojoba oil, castor oil, or also olive oil, soya oil, and the derivatives thereof. Mineral oils such as paraffin oil and petrolatum are suitably contained within the scope of the present invention. It should as well be noted that compositions of the present invention can contain mixture of one or more natural oils and mineral oil.

Further, suitable synthetic oil components are in particular fatty alcohol fatty acid esters such as isopropyl myristate, palmitate, stearate and isostearate, oleyl oleate, isocetyl stearate, hexyl laurate, dibutyl adipate, dioctyl adipate, myristyl myristate, oeyl erucate, polyethylene glycol and polyglyceryl fatty acid esters, cetyl palmitate and hydrogenated polyisobutene.

Synthetic ones are those of silicone oils. Here again any silicone oil either volatile and/or non-volatile is suitable for the compositions of the present invention. Preferred silicone oils are non-volatile silicone oils known with their INCI name as dimethicone and dimethiconol. Volatile silicone oils such as cyclomethicones may be used in combination with non-volatile silicones and/or other wax and/or oils mentioned above. Commercially, they are available from various companies for example Dow Corning with the known DC series, Wacker Chemie and Toray silicones. All commercially available non volatile silicones are suitable in the compositions of the present invention. Examples to those are DC 200 series, DC1401, DC 1403, DC 1501 and DC 1503. Furthermore, aminated silicones such as amodimethicone and arylated silicones comprising at least one aryl group in its molecule such as phenyl methicone, phenyl trimethicone, diphenyl dimethicone, diphenylsiloxy phenyl trimethicone, tetramethyl tetraphenyl trisiloxane, triphenyl trimethicone, tetramethyl tetraphenyl trisiloxane and trimethyl pentaphenyl trisiloxane can be advantageously comprised in the compositions of the present invention.

Concentration of one or more oil in the compositions of the present invention may be in the range of 0.1 to 30% by weight, preferably 0.2 to 25% by weight and more preferably 1 to 22.5% by weight, calculated to the total of the composition.

The compositions according to the invention may also comprise further agents, such as proteins, for example bamboo protein, and protein hydrolyzates and polypeptides, e.g. keratin hydrolyzates, collagen hydrolyzates of the type "Nutrilan®" or elastin hydrolyzates, as well as, in particular vegetable, optionally cationized protein hydrolyzates, for example "Gluadin®".

Additionally natural plant extracts can as well form part of the compositions of the present invention. Those are incorporated usually in an amount of about 0.01% to about 5%, preferably 0.05% to 3.5%, in particular 0.1% to 2% by weight, calculated to the total of the composition . Suitable one are especially those non-aqueous ones such as alcoholic plant extracts known per se are in particular extracts from leaves, fruits, blossoms, roots, rinds or stems of aloe, pineapple, artichoke, arnica, avocado, valerian, bamboo, henbane, birch, stinging nettle, echinacea, ivy, wild angelica, gentian, ferns, pine needles, silver weed, ginseng, broom, oat, rose hip, hamamelis, hay flowers, elderberry, hop, coltsfoot, currants, chamomile, carrots, chestnuts, clover, burr root, coconut, cornflower, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn, etc. They are available commercially from various suppliers.

Compositions of the present invention may comprise UV filters either for stabilization of the product colour, if any, and/or for protection of hair from environmental influences such as loss of elasticity, loss of hair colour (bleaching effect of sun light). Suitable UV-absorbing substance are Polysilicone-15, 4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2,4-dihydroxybenzophenone, 2,2',4,4'-tetrahydroxy-benzophenone, 2-hydroxy-4-methoxybenzophenone and its 5-sulfonic acid or the sodium salt thereof, 2,2'-dihydroxy-4,4'-dimethoxybenzophenone, 2-hydroxy-5-chlorobenzophenone, 2,2'-dihydroxy-4-methoxybenzophenone, 2,2'-dihydroxy-4,4'-dimethoxy-5,5'-disulfobenzophenone or the sodium salt thereof, 2-hydroxy-4-octyloxybenzophenone, 2-hydroxy-4-methoxy-4'-methylbenzophenone, 3-benzyl-idenecampher, 3-(4'-sulfo)-benzyl-idenebornane-2-one and the salts thereof and/or 3-(4'-methyl benzylidene)-DL-campher, and/or polysiliocne-15.

The total concentration of UV filters in the composition is in the range of 0.01 to 2.5% by weight, preferably 0.1 to 2% by weight and more preferably 0.1 to 1.5% by weight, calculated to the total of the composition.

The compositions of the present invention can contain one or more organic solvents within the scope of the invention, Suitable ones are ethanol, propanol, isopropanol, isopentane, benzyl alcohol, benzyloxyethanol, alkylene carbonates such as ethylene carbonate and propylene carbonate, phenoxyethanol, butanol, isobutanol, cyclohexane, cyclohexanol, ethylenecarbonate, ethyleneglycol monoethylether, ethylene glycol monobutyl ether, ethylene glycol monophenyl ether, 1-phenylethylalcohol, 2-phenylethylalcohol, o-methoxyphenol. The most preferred organic solvents are ethanol, isopropanol and propanol. Concentration of solvents is in the range of 0 to 20% and preferably 1 to 15%, more preferably 1 to 10% and most preferably 2 to 10% by weight, calculated to total of the composition.

In a further embodiment of the present invention, the compositions comprise one or more pigments and/or direct dyes for colouring hair and/or for colouring the composition. Suitable direct dyes are cationic, anionic, neutral dyes and their mixtures as available commercially from various suppliers and used mainly in semipermanent hair coloration.

Non-limiting examples to cationic dyes are Basic Blue 6, Basic Blue 7, Basic Blue 9, Basic Blue 26, Basic Blue 41, Basic Blue 99, Basic Brown 4, Basic Brown 16, Basic Brown 17, Basic Orange 31, Natural Brown 7, Basic Green 1, Basic Red 2, Basic Red 12 Basic Red 22, Basic Red 51, Basic Red 76, Basic Violet 1, Basic Violet 2, Basic Violet 3, Basic Violet 10, Basic Violet 14, Basic Yellow 57 and Basic Yellow 87.

Further suitable direct dyes are anionic dye. Suitable non-limiting examples are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

Further suitable dyes for colouring hair within the meaning of the present invention are those of neutral nitro dyes. Suitable non-limiting examples are HC Blue No.2, HC Blue No.4, HC Blue No.5, HC Blue No.6, HC Blue No.7, HC Blue No.8, HC Blue No.9, HC Blue No.10, HC Blue No.11, HC Blue No.12, HC Blue No.13, HC Brown No.1, HC Brown No.2, HC Green No.1, HC Orange No.1, HC Orange No.2, HC Orange No.3, HC Orange No.5, HC Red BN, HC Red No.1, HC Red No.3, HC Red No.7, HC Red No.8, HC Red No.9, HC Red No.10, HC Red No.11, HC Red No.13, HC Red No.54, HC Red No.14, HC Violet BS, HC Violet No.1, HC Violet No.2, HC Yellow No.2, HC Yellow No.4, HC Yellow No.5, HC Yellow No.6, HC Yellow No.7, HC Yellow No.8, HC Yellow No.9, HC Yellow No.10, HC Yellow No.11, HC Yellow No.12, HC Yellow No.13, HC Yellow No.14, HC Yellow No.15, 2- Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Plant dyestuffs may also be used as hair colorant within the meaning of the present invention for example henna (red or black), alkanna root, laccaic acid, indigo, logwood powder, madder root, caramel and rhubarb powder, etc.

The above mentioned dyestuffs are also used, especially the anionic ones, for product coloring at reduced concentrations.

The pigments may be organic or inorganic ones. Suitable non-limiting examples to organic ones are salts of carmine, aniline black, azo yellow, quinacridone, phthalocyanin blue, sorghum red, CI42090, CI69800, CI69825, CI73000, CI74100, CI74160, CI11680, CI11710, CI15985, CI19140, CI20040, CI21100, CI21108, CI47000, CI47005, CI61565, CI61570, CI74260, CI11725, CI15510, CI45370, CI71105, CI 12085, CI12120, CI12370, CI12420, CI12490, CI14700, CI15525, CI15580, CI15620, CI15630, CI15800, CI15850, CI15865, CI15880, CI17200, CI26100, CI45380, CI45410, CI58000, CI73360, CI73915, CI75470, and/or their mixtures, and/or organic dye-adsorbed lakes such as organic lakes of barium, strontium, calcium or aluminium, lakes based on cochineal carmine which are known as Blue 1 lake, Yellow 7 lake, Green 3 lake, Orange 4 Lake, Orange 5 Lake, Orange 10 Lake, Red 4 Lake, Red 6 Lake, Red 7 Lake, Red 21 Lake, Red 22 Lake, Red 27 Lake, Red 28 Lake, Red 30 Lake, Red 31 Lake, Red 33 Lake, Red 34 Lake, Red 40 Lake, Yellow 5 Lake, Yellow 6 Lake, Yellow 7 Lake, Yellow 10 Lake, and/or their mixtures.

Suitable inorganic pigments are mica, black iron oxide, carbon black, black titanium oxide, red iron oxide, yellow iron hydroxide, titanium iron oxide, titanium dioxide, manganese violet, ultramarine blue, chromium oxides, hydrated chromium oxides, ferric blue, zirconium oxide, bismuth oxychloride, bismuth citrate, zinc oxide, cerium oxide, silicon dioxide, aluminium, alimunium oxide hydrate, aluminium silicate, barium sulfate, calcium carbonate, calcium sulfate, cobalt aluminium oxide, copper powder, gold powder, Prussion blue, magnesium carbonate, manganese (II) phosphate, bronze powder, silver powder, ferric ammonium ferrocyanide, ferric ferrocyanide, henna, zinc sulphide, and/or their mixtures.

The total concentration of direct dyes and/or pigments in the compositions of the present invention is in the range of 0.001 to 10%, preferably 0.01 to 7.5% and more preferably 0.05 to 6%, and most preferably 0.1 to 5% by weight, calculated to the total of the composition.

Furthermore compositions of the present invention can comprise all substances customarily found in such preparations. Examples of such substances are preservatives, fragrances, etc.

The following examples are to illustrate the invention but not to limit.

EXAMPLE 1

| | % by weight |
|---|---|
| Beeswax | 59.0 |
| Calcium sulphate | 20.0 |
| Laureth-38 | 20.0 |
| Fragrance | 1.0 |

The above composition was prepared by melting Beeswax and Laureth-38 in a vessel at 70° C. and afterwards dispersing calcium sulphate in the melted mixture at 70° C. The preparation was cooled down to around 45° C. and fragrance was added and the batch was quickly cooled down to around 35° C. under continuous mixing.

The same composition was produced with the same amount of Diatomaceous Earth in the same way. Both were tested using a hair streak by applying the same amount of the product, 0.25 g/g hair. A photograph of the streaks is presented as FIG. 1. The streak A was untreated streak, the streak B was treated with the comparative composition and the streak C was treated with the Example 1.

From the picture is beyond any doubt that the hair treated with the comparative composition comprises hair fibre aggregates and appears to be streaky whereas the streak C does not comprise any hair fibre aggregate and appears loose, natural and more attractive.

Similar results were observed with the following examples.

EXAMPLE 2

| | % by weight |
|---|---|
| Beeswax | 54.0 |
| Calcium sulphate | 20.0 |
| Laureth-38 | 20.0 |
| Isobutylene/ethylmaleimide/hydroxyethylmaleimide Copolymer | 5.0 |
| Fragrance | 1.0 |

The above composition was prepared by melting Beeswax and Laureth-38 in a vessel at 70° C. and afterwards dispersing calcium sulphate in the melted mixture at 70° C. The preparation was cooled down to around 45° C. and the polymer and fragrance were added and the batch was quickly cooled down to around 35° C. under continuous mixing.

The above composition was applied onto freshly cleansed dry hair. It was observed that hair feels soft, smooth and bodified, and appears textured and natural, and comprises no hair fibre aggregates.

EXAMPLE 3

| | % by weight |
|---|---|
| Beeswax | 44.0 |
| Ozokerit | 10.0 |
| Calcium sulphate | 20.0 |
| PEG-40 hydrogenated castor oil | 20.0 |
| VP/VA copolymer | 5.0 |
| Fragrance | 1.0 |

Similar results were observed as in the Example 2.

EXAMPLE 4

| | % by weight |
|---|---|
| Beeswax | 42.0 |
| Ozokerit | 12.0 |
| Calcium sulphate | 12.0 |
| Dimethicone | 2.0 |
| Diatomaceous Earth | 5.0 |
| PEG-40 hydrogenated castor oil | 20.0 |
| VP/VA copolymer | 6.0 |
| Fragrance | 1.0 |

Similar results were observed as in the Example 2.

EXAMPLE 5

| | % by weight |
|---|---|
| Paraffin | 43.0 |
| Calcium sulphate | 5.0 |
| Diatomaceous Earth | 26.0 |
| PEG-40 hydrogenated castor oil | 20.0 |
| VP/VA copolymer | 5.0 |
| Fragrance | 1.0 |

Similar results were observed as in the Example 2.

EXAMPLE 6

| | % by weight |
|---|---|
| Carnauba Wax | 33.0 |
| Paraffinum Liquidum | 5.0 |
| Calcium sulphate | 6.0 |
| Diatomaceous Earth | 30.0 |
| PEG-60 hydrogenated castor oil | 20.0 |
| Ethylhexyl Methoxycinnamate | 0.1 |
| VP/VA copolymer | 4.9 |
| Fragrance | 1.0 |

EXAMPLE 7

| | % by weight |
|---|---|
| Microwax | 32.0 |
| Olive oil | 5.0 |
| Silica | 5.0 |
| Calcium Sulfate | 10.0 |
| Diatomaceous Earth | 22.0 |
| PEG-40 hydrogenated castor oil | 20.0 |
| Ethylhexyl Methoxycinnamate | 0.1 |
| VP/VA copolymer | 4.9 |
| Fragrance | 1.0 |

EXAMPLE 8

| | % by weight |
|---|---|
| Microwax | 33.0 |
| Olive oil | 5.0 |
| Silica | 5.0 |
| Ozokerit | 5.9 |
| Calcium Sulfate | 30.0 |
| PEG-40 hydrogenated castor oil | 20.0 |
| Benzophenone-3 | 0.1 |
| Fragrance | 1.0 |

EXAMPLE 9

| | % by weight |
|---|---|
| Microwax | 33.0 |
| Carnauba Wax | 24.0 |
| Hydrogenated Polyisobutene | 10.0 |
| Iron Oxide | 2.0 |
| Calcium Sulfate | 5.0 |
| PEG-40 hydrogenated castor oil | 20.0 |
| Ethylhexyl Methoxycinnamate | 0.1 |
| VP/VA copolymer | 4.9 |
| Fragrance | 1.0 |

EXAMPLE 10

| | % by weight |
|---|---|
| Carnauba Wax | 33.0 |
| Cetearyl alcohol | 15.0 |
| Paraffinum Liquidum | 5.0 |
| Calcium sulphate | 11.0 |
| Diatomaceous Earth | 10.0 |
| PEG-60 hydrogenated castor oil | 20.0 |
| Ethylhexyl Methoxycinnamate | 0.1 |
| VP/VA copolymer | 4.9 |
| Fragrance | 1.0 |

The invention claimed is:

1. A hair conditioning and/or styling composition comprising:

a mixture of:

one or more fatty substances and/or waxes solid at 20° C.; and one or more surfactants; and calcium sulphate particles dispersed in the mixture, wherein the hair conditioning and/or styling compostion is a leave-in composition and does not comprise water at a total concentration higher than or equal to 5% by weight, calculated to a total weight of the hair conditioning and/or styling composition, the one or more fatty substances and/or waxes solid at 20° C. is selected from the group consisting of ozokerit, carnauba wax, parrafin, lanolin wax, candelila wax, bees wax, microcrystalline wax and fatty alcohols, and a mixture thereof, the one or more fatty substances and/or waxes sold at 20° C. are present at a total concentration in a range of 20 to 70% by weight, calculated to the total weight of the hair conditioning and/or styling composition, and the calcium sulphate particles have a particle size below 200 μm measured with sieve analysis and are present in the hair conditioning and/or styling composition at a total concentration in a range of 7.5 to 35% by weight, calculated to the total weight of the hair conditioning and/or styling composition.

2. The hair conditioning and/or styling composition according to claim 1, wherein the total concentration of the one or more fatty substances and/or waxes solid at 20° C. is in the range of 25 to 70% by weight, calculated to the total weight of the hair conditioning and/or styling composition.

3. The hair conditioning and/or styling composition according to claim 1, further comprising one or more non-ionic surfactants selected from the group consisting of from one or more fatty alcohol ethoxylates, one or more monoglycerides and one or more of their ethoxylates, one or more ethoxylated oils, one or more long-chain fatty acid mono- and dialkanolamides, one or more alkyl polyglucosides, sorbitan esters, and a mixture thereof.

4. The hair conditioning and/or styling composition according to claim 3, wherein the one or more non-ionic surfactants is present in the hair conditioning and/or styling composition at a total concentration in a range of 2 to 35% by weight, calculated to the total of the hair conditioning and/or styling composition.

5. The hair conditioning and/or styling composition according to claim 1, further comprising one or more additional inert pulverulent material present in the hair conditioning and/or styling composition at a total concentration in a range of 2 to 35% by weight, calculated to the total weight of the hair conditioning and/or styling composition.

6. The hair conditioning and/or styling composition according to claim 5, wherein the one or more additional inert pulverulent material is selected from the group consisting of Diatomaceous Earth, kaolin, silicum dioxide, starch, titanium dioxide, and a mixture thereof.

7. The hair conditioning and/or styling composition according to claim 1, further comprising one or more hair styling polymers selected from anionic polymers, cationic polymers, non-ionic polymers, and amphoteric polymers and present in the composition at a total concentration in a range of 0.1 to 25% by weight, calculated to the total weight of the hair conditioning and/or styling composition.

8. The hair conditioning and/or styling composition according to claim 1, further comprising at least one selected from synthetic oil and natural oil present in the hair conditioning and/or styling composition at a total concentration in a range of 0.1 to 30% by weight, calculated to the total weight of the hair conditioning and/or styling composition.

9. The composition according to claim 1, further comprising one or more ingredients selected from the group consisting of:

one or more UV filters, one or more proteins and one or more of their hydrolysates;

one or more natural plant extracts;

one or more organic solvents;

one or more pigments;

one or more direct dyes; and a mixture thereof.

* * * * *